(12) United States Patent
Nishijima et al.

(10) Patent No.: US 6,568,847 B2
(45) Date of Patent: May 27, 2003

(54) JUDGING METHOD AND PROCESSING APPARATUS

(75) Inventors: Yuuichi Nishijima, Kumamoto (JP); Kouji Okamura, Kumamoto (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 09/916,503

(22) Filed: Jul. 30, 2001

(65) Prior Publication Data

US 2002/0027942 A1 Mar. 7, 2002

(30) Foreign Application Priority Data

Jul. 31, 2000 (JP) .................................... 2000-230988

(51) Int. Cl.$^7$ ............................................. G01N 25/00
(52) U.S. Cl. ........................................ 374/45; 165/11.1
(58) Field of Search ........................... 374/45; 165/11.1; 414/936, 937

(56) References Cited

U.S. PATENT DOCUMENTS

| | | | | |
|---|---|---|---|---|
| 5,491,423 A | * | 2/1996 | Turetta .................... | 219/447.1 |
| 5,669,752 A | * | 9/1997 | Moon ....................... | 198/394 |
| 5,756,964 A | * | 5/1998 | Hsu et al. ................. | 118/728 |
| 5,948,986 A | * | 9/1999 | Brown ...................... | 361/234 |
| 5,961,774 A | * | 10/1999 | Tamura et al. ............. | 118/500 |
| 6,075,375 A | * | 6/2000 | Burkhart et al. ........... | 324/662 |
| 6,217,212 B1 | * | 4/2001 | Brenninger et al. ........ | 374/123 |
| 6,377,060 B1 | * | 4/2002 | Burkhart et al. ........... | 324/662 |
| 6,403,322 B1 | * | 6/2002 | Fischer ..................... | 435/6 |

* cited by examiner

Primary Examiner—Diego Gutierrez
Assistant Examiner—Lydia M. De Jesús
(74) Attorney, Agent, or Firm—Oblon, Spivak, McClelland, Maier & Neustadt, P.C.

(57) ABSTRACT

The present invention is a method of judging whether a substrate is accurately placed at a predetermined position when placing the substrate at the predetermined position on a plate to perform heat treatment or cooling treatment therefor.

The present invention has the step of measuring temperature of the plate at least from a first point of time to a second point of time during which the plate temperature changes, after placing the substrate at the plate, the step of calculating a temperature integrated area I determined by a range enclosed the measured temperature curve changing in time sequence and a set temperature of the plate, and the step of comparing the calculated temperature integrated area I with threshold values of a temperature integrated area set in advance.

13 Claims, 10 Drawing Sheets

JUDGING METHOD AND PROCESSING APPARATUS

BACKGROUND OF THE INVENTION

1. Field of the Invention

The present invention relates to a judging method and a processing apparatus.

2. Description of the Related Art

In the photolithography process in fabricating a semiconductor device, various kinds of heat treatments such as a heat treatment (pre-baking) performed after a resist solution is applied to a front surface of a semiconductor wafer (hereinafter called "the wafer"), a heat treatment (post-exposure baking) after the pattern is exposed, and the like are performed.

The aforementioned heating treatments are usually performed by heat treatment units. As shown in FIG. 13, a heating treatment unit 100 is provided with a thick disk-shaped heating plate 101 for placing a wafer W at a predetermined position thereon to heat it. Support pins 102 for supporting the wafer W are provided at the aforementioned placement position on the heating plate 101, so that the wafer W is prevented from being in direct contact with the heating plate 101 when the wafer W is placed thereat. Hoisting and lowering pins 103 for hoisting and lowering the wafer W when the wafer W is placed at the heating plate 101 are provided under the heating plate 101 so as to penetrate through the heating plate 101.

Since the wafer W needs to be heated uniformly within the wafer W surface, it is important to place the wafer W horizontally at the predetermined position when placing the wafer W on the heating plate 101. Thus, a plurality of guide members 105 having inclined planes 104 facing the placement position of the wafer W are provided on the heating plate 101 so as to surround the aforementioned placement position for the wafer W. According to the above structure, when the wafer W is heated, the wafer W transferred from another treatment unit is supported on the hoisting and lowering pins 103 protruded above the heating plate 101 and waiting in advance, and when the hoisting and lowering pins 103 are lowered, the wafer W is lowered and placed on the support pins 102 on the heating plate 101. When the wafer W is placed thereon, if the wafer W is placed out of the predetermined placement position to some extent, it is guided to the accurate position by the inclined planes 104 of the aforementioned guide members 105 as shown in FIG. 14.

However, when the wafer W is deviated from the placement position to a large extent, for example, when the wafer W is placed in such a manner that it rides on the guide member 105, the wafer W is heat-treated in this state, thus causing a defective product due to poor heating. When larger dust than the support pin 102 adheres to the heating plate 101, the wafer W rides on the dust, and poor heating also occurs.

The occurrence of such a defect is usually found in a detecting step to be performed later. However, since many of the aforementioned defects occur successively, it frequently happens that many defective products have already made when the occurrence of a defect is found in the aforementioned detecting step, and therefore it is desired that the occurrence of the aforementioned defects is detected in the earlier step before the damage becomes too heavy.

It is recognized that when the wafer W is placed at the aforementioned heating plate 101, the wafer W at a low temperature takes the heat, and the temperature of the heating plate is reduced temporarily. When the wafer W is not accurately placed thereat, or for example, when the wafer W is obliquely placed thereat, the distance between the heating plate 101 and the wafer W becomes larger, and heat conduction is reduced, thus making the aforementioned temperature reduction smaller. Thus, it is considered to detect whether or not the wafer W is properly placed by utilizing the change in temperature reduction of the heating plate when the wafer W is placed thereat.

However, on this occasion, when it is determined whether or not the wafer is placed properly, for example, based on the lowest temperature during the time in which the heating plate temperature reduces, the lowest temperature has a wide range of variation. Accordingly, it is desired to improve the reliability.

SUMMARY OF THE INVENTION

The present invention is made in view of the aforementioned point, and its object is to provide a method for promptly and accurately judging whether a substrate such as a wafer is accurately placed at a heating plate or not and a processing apparatus capable of carrying out the method in order to reduced the occurrence of the defect of the wafer to a minimum.

In order to attain the aforementioned object, the present invention is a method of judging whether a substrate is accurately placed at a predetermined position when placing the substrate at the predetermined position on a plate to perform heat treatment or cooling treatment therefor, and has the step of setting the aforementioned plate at a predetermined temperature, the step of measuring temperature of the plate at least from a first point of time to a second point of time during which the plate temperature changes, after placing the substrate on said plate, the step of calculating a temperature integrated area I determined by a range enclosed by the measured temperature curve changing in time sequence and a set temperature of the aforementioned plate, and the step of comparing the calculated temperature integrated area I with a threshold value of a temperature integrated area previously set.

According to another aspect of the invention, the present invention is a method of judging whether a substrate is accurately placed at a predetermined position when placing the substrate at the predetermined position on a plate to perform heat treatment or cooling treatment therefor, and has the step of setting the aforementioned plate at a predetermined temperature, the step of measuring temperature of the plate at least from a first point of time to a second point of time during which the plate temperature changes, after placing the substrate on the aforementioned plate, and the step of comparing the measured temperature with threshold values related to standard deviation of the plate temperature in a case in which the substrate is accurately placed.

According to still another aspect of the present invention, the present invention is a method of judging whether a substrate is accurately placed at a predetermined position when placing the substrate at the predetermined position on a plate to perform heat treatment or cooling treatment therefor, and has the step of setting the aforementioned plate at a predetermined temperature, the step of measuring temperature of the plate at least from a first point of time to a second point of time during which the plate temperature changes, after placing the substrate on the aforementioned plate, and the step of comparing a maximum temperature difference from the measured temperature with a previously set threshold value related to standard deviation of a maximum temperature difference of the plate temperature in a case in which the substrate is accurately placed. As the aforementioned measured temperature which is compared, for example, the lowest temperature when the plate temperature is reduced to the lowest as a result of the substrate being placed thereat is proposed in case of heat treatment, and the highest temperature when the plate temperature rises to the highest as a result of the substrate being placed thereat is proposed in case of cooling treatment.

The aforementioned temperature measurement may be performed at a plurality of positions on the plate, and the aforementioned comparing step may be performed for each measurement position. By measuring the temperature at a plurality of positions on the heating plate as this, more reliable judgement as to whether the aforementioned substrate is accurately placed or not can be made.

A processing apparatus of the present invention is, in a processing apparatus having a plate for placing a substrate at a predetermined position thereon to heat or cool the substrate at a predetermined temperature, has a temperature sensor for measuring temperature of the aforementioned plate, and a processor for calculating a temperature integrated area I determined by a range enclosed by a measured temperature curve changing in time sequence and a set temperature of the aforementioned plate, based on the measured result of the plate temperature from a first point of time to a second point of time during which the plate temperature changes, after the substrate is placed at the aforementioned plate, which is measured by the aforementioned temperature sensor, and for comparing the temperature integrated area I with threshold values of a temperature integrated area previously set.

Further, according to another aspect of the invention, a processing apparatus of the present invention is a processing apparatus having a plate for placing a substrate at a predetermined position thereon to heat or cool the substrate at a predetermined temperature, and has a temperature sensor for measuring temperature of the aforementioned plate, and means for comparing measured temperature of the aforementioned temperature sensor with a previously set threshold values related to standard deviation of the plate temperature in a case in which the substrate is accurately placed.

According to the present invention, after the substrate is placed at the plate for heating or cooling, the temperature during a period of time when the temperature of the plate reduces or rises is measured, and the temperature integrated area I enclosed by the measured temperature curve in time sequence and the set temperature of the heating plate is calculated. The temperature integrated area in the case in which the substrate is accurately placed is obtained in advance, and the aforementioned temperature integrated area I is compared with the threshold values being allowable values of the ideal temperature integrated area. As a result of the above, when the temperature integrated area I measured and calculated exceeds the aforementioned threshold values, it can be judged that the substrate is not accurately placed. Accordingly, it can be judged whether or not the substrate is accurately placed at the heating plate and heat-treated properly in the earlier step. As the reference for judgement, the temperature integrated area I is used, thus making it possible to make more reliable judgment without being influenced by an instant temperature change and the like due to other factors as compared with when, for example, the lowest temperature of the heating plate is simply used as the reference.

The threshold values of the aforementioned temperature integrated area may be related to standard deviation of the temperature integrated area in a case in which the substrate is accurately placed at the aforementioned predetermined position. As described above, the data of the temperature integrated area in the case in which the substrate is accurately placed at the aforementioned predetermined position is collected in advance, and, for example, the standard deviation of the data is set as the aforementioned threshold values, whereby the aforementioned data that has to be collected in advance is only the temperature integrate area in the case in which the aforementioned substrate is accurately placed. That is, when the standard deviation is not used, the data in the case in which the substrate is accurately placed and the data in the case in which the substrate is not accurately place has to be collected, and the threshold values have to be determined from both the data, whereby much time and effort are spent in collecting the data. Consequently, according to the present invention, it is sufficient if only one kind of data is collected, thus making it possible to reduce working time and effort of an operator. What is related to the standard deviation is, for example, N σ (N is a real number), and the standard deviations σ, 2 σ, 3 σ and the like are adopted.

DETAILED DESCRIPTION OF THE PREFERRED EMBODIMENT

Figure 1:
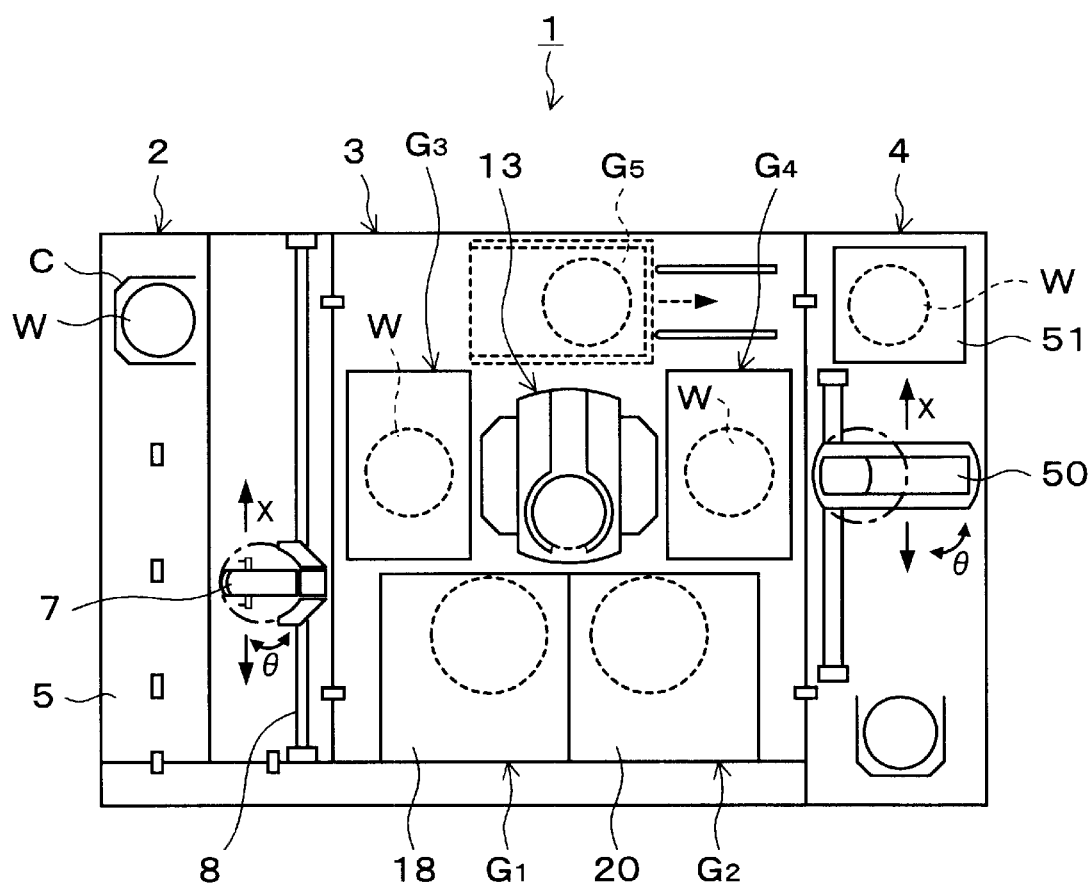
FIG. 1 is a plan view showing an outline of a configuration of a coating and developing treatment system having a PEB unit according to an embodiment of the present invention.
Figure 2:
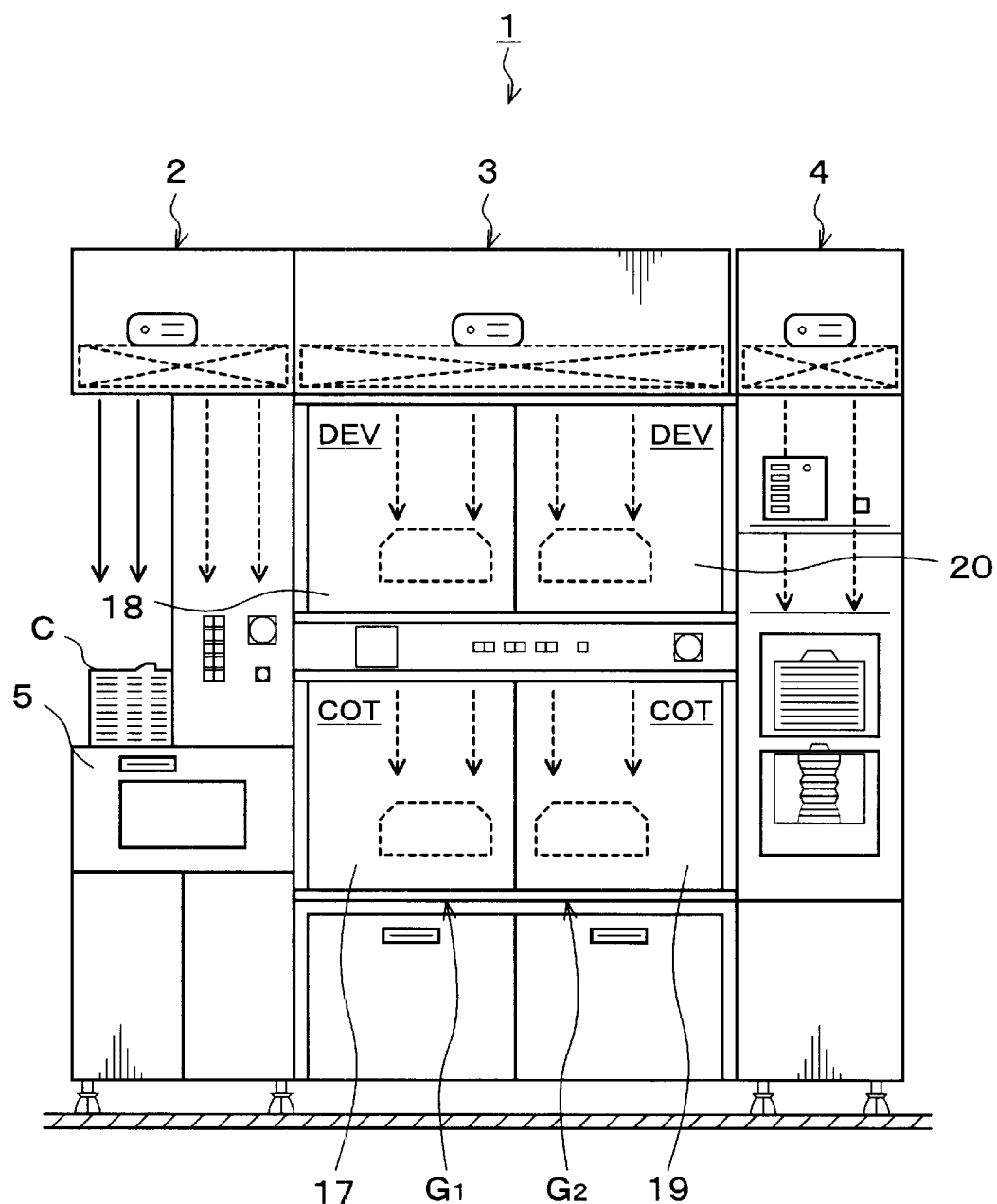
FIG. 2 is a front view of the coating and developing treatment system in FIG. 1.
Figure 3:
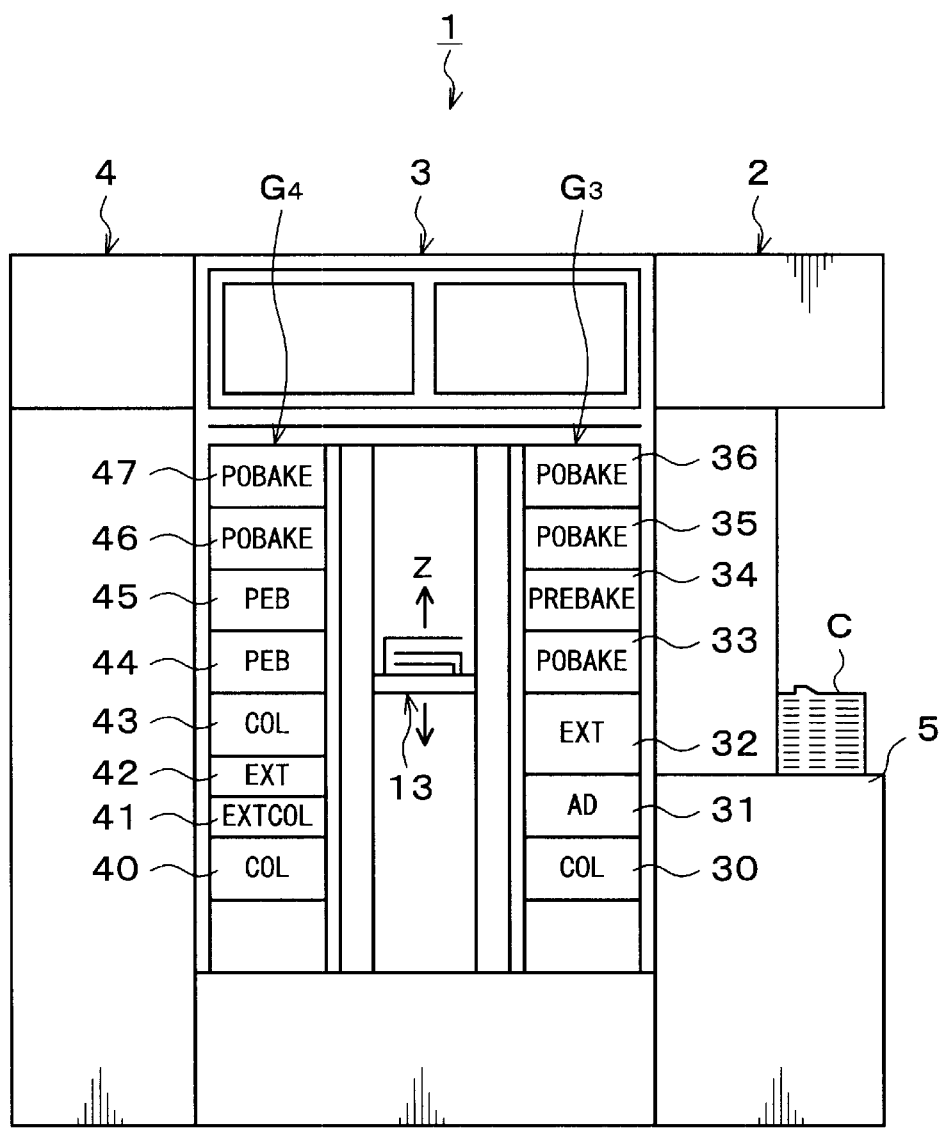
FIG. 3 is a rear view of the coating and developing treatment system in FIG. 1.

A preferred embodiment of the present invention will be explained below. A processing apparatus according to this embodiment is carried out as a heat treatment unit. FIG. 1 is a plan view of a coating and developing treatment system 1 having the aforementioned heat treatment unit, FIG. 2 is a front view of the coating and developing treatment system 1, and FIG. 3 is a rear view of the coating and developing treatment system 1.

As shown in FIG. 1, the coating and developing treatment system 1 has a structure in which a cassette station 2 for carrying, for example, 25 wafers W per cassette, as a unit, from/to the outside into/out of the coating and developing treatment system 1 and carrying the wafer W into/out of a cassette C, a processing station 3 in which various kinds of treatment units each for performing predetermined treatment for the wafers one by one in coating and developing treatment processes are stacked in multiple tiers, and an interface section 4 for delivering the wafer W from/to an aligner not illustrated but provided adjacent to the processing station 3 are integrally connected.

In the cassette station 2, a plurality of cassettes C can be mounted at predetermined positions on a cassette mounting table 5 which is a mounting portion in a line in an X-direction (a top-to-bottom direction in FIG. 1). A wafer carrier 7 which is movable in the direction of arrangement of the cassettes (the X-direction) and in the direction of arrangement of the wafers W housed in the cassette C (a Z-direction; a vertical direction) is provided to be movable along a carrier guide 8 so as to be selectively accessible to each cassette C.

The wafer carrier 7 has an alignment function of aligning the wafer W. The wafer carrier 7 is structured to be accessible also to an extension unit 32 included in a third treatment unit group G3 on the processing station 3 side as will be described later.

In the processing station 3, a main carrier unit 13 is provided at the center thereof, and various kinds of treatment units are stacked in multiple tiers around the main carrier unit 13 to compose treatment unit groups. In the coating and developing treatment system 1, four treatment unit groups G1, G2, G3, and G4 are disposed. The first and second treatment unit groups G1 and G2 are disposed on the front side of the coating and developing treatment system 1, the third treatment unit group G3 is disposed adjacent to the cassette station 2, and the fourth treatment unit group G4 is disposed adjacent to the interface section 4. Further, a fifth treatment unit group G5 shown by a broken line can be additionally disposed on the rear side as an option. The aforementioned main carrier unit 13 can carry the wafer W into/out of various treatment units which are arranged in the treatment unit groups G1, G2, G3, G4 and G5 and will be described later. It should be noted that the number and disposition of the treatment unit groups are different depending on the type of treatment performed for the wafer W, and the number of treatment unit groups may not be necessarily four, if only it is one or more.

In the first treatment unit group G1, for example, as shown in FIG. 2, a resist coating unit 17 for coating the wafer W with a resist solution and a developing treatment unit 18 for performing developing treatment for the wafer W after exposure are stacked in two tiers from the bottom in order. Similarly, in the second treatment unit group G2, a resist coating unit 19 and a developing treatment unit 20 are stacked in two tiers from the bottom in order.

In the third treatment unit group G3, for example, as shown in FIG. 3, a cooling unit 30 for performing cooling treatment for the wafer W, an adhesion unit 31 for enhancing the adhesion of the resist solution and the wafer W, an extension unit 32 for making the wafer W wait therein, pre-baking units 33 and 34 each for drying a solvent in the resist solution, post-baking units 35 and 36 each for performing heating treatment after the developing treatment, or the like are stacked, for example, in seven tiers from the bottom in order.

In the fourth treatment unit group G4, for example, a cooling unit 40, an extension and cooling unit 41 for naturally cooling the wafer W placed therein, an extension unit 42, a cooling unit 43, post-exposure baking units 44 and 45 (hereinafter called "PEB units") as the heat treatment unit according to this embodiment, post-baking units 46 and 47, or the like are stacked, for example, in eight tiers from the bottom in order.

A wafer carrier 50 is provided at the center portion of the interface section 4. The wafer carrier 50 is structured to be movable in the X-direction (the top-to-bottom direction in FIG. 1) and in the Z-direction (the vertical direction) and rotatable in a θ-direction (a direction of rotation around a Z-axis) so as to access the extension and cooling unit 41 and the extension unit 42 included in the fourth treatment unit group G4, a periphery exposure unit 51, and the aligner not illustrated to carry the wafer W to each of them.

Figure 4:
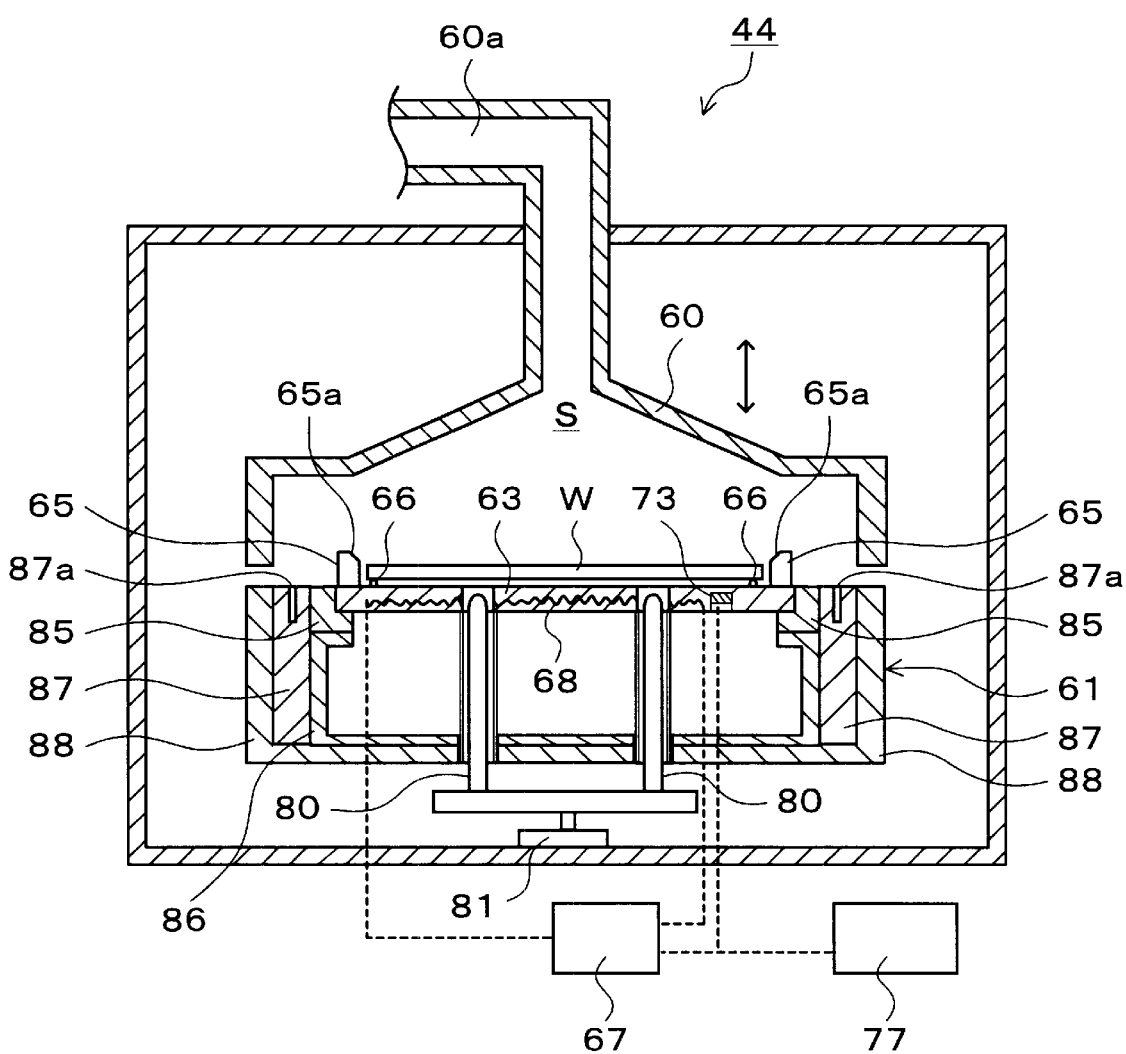
FIG. 4 is an explanatory view of a vertical section of the PEB unit according to the present embodiment.

Next, the structure of the aforesaid PEB unit 44 will be explained. As shown in FIG. 4, the PEB unit 44 has a lid body 60 placed at an upper side and movable up and down, and a heating plate housing part 61 placed at an lower side and integrated with the lid body 60 to form a treatment chamber S.

The lid body 60 has an almost conical form gradually raised higher toward a center portion, and is provided with an exhaust portion 60a at a top portion. An atmosphere inside the treatment chamber S is uniformly exhausted from the exhaust portion 60a. The heating plate housing part 61 is provided with a thick disk-shaped heating plate 63 for placing the wafer W at a predetermined position thereon and heating it.

Figure 5:
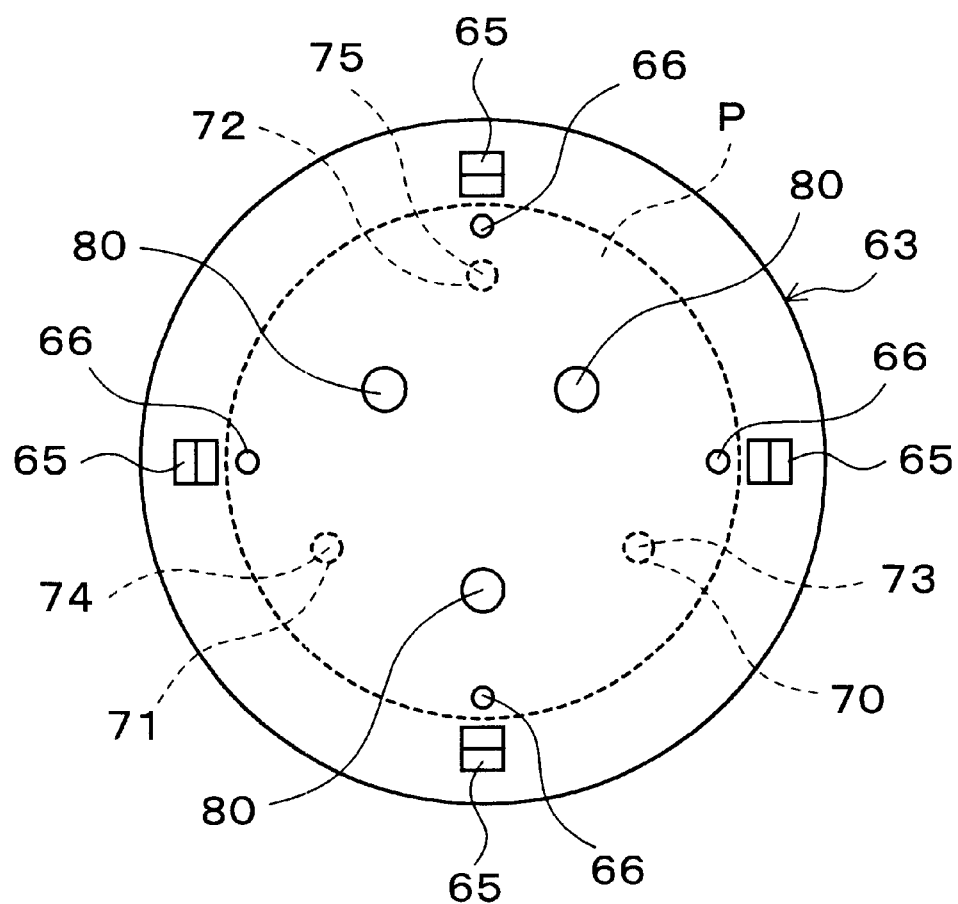
FIG. 5 is a plan view of a heating plate of the PEB unit in FIG. 4.
Figure 6:
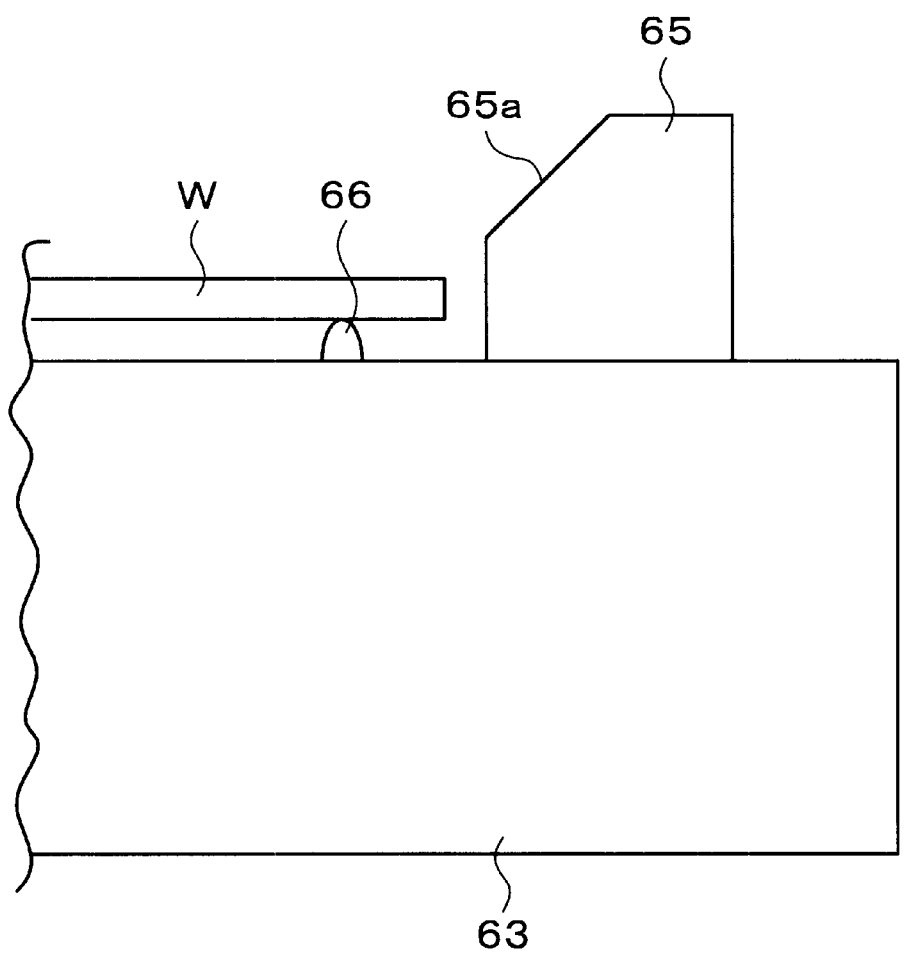
FIG. 6 is an explanatory view in a vertical section showing a guide member on the heating plate in FIG. 5.

A guide member 65 as a guide member for placing the wafer W at a predetermined position P as shown in FIG. 5 is provided on the heating plate 63. The guide members 65 are each provided at a plurality of spots, for example, at four spots so as to surround the predetermined position P. The guide member 65 has an inclined portion 65a at the predetermined position P side as shown in FIG. 6, and when an edge portion of the wafer W is accidentally placed on the inclined portion 65a, the wafer W slips off the inclined portion 65a to be placed at the predetermined position P.

Support pins 66 for supporting the wafer W when the wafer W is placed are each provided at a plurality of spots on the heating plate 63 as shown in FIG. 4 and FIG. 5, so that the wafer W is prevented from being in direct contact with the heating plate 63.

The heating plate 63 incorporates a heater 68 controlled by a heater controller 67 as shown in FIG. 4, and the heating plate 63 is heated to a set temperature $T_0$ by heat generated from the heater 68 so that the wafer W can be heated to the predetermined temperature $T_0$.

Holes 70, 71 and 72 having bottoms with a predetermined depth are each provided at three spots equally spaced from each other from an underside to a front face of the heating plate 63 in a predetermined position P of the heating plate 63, for example, at each predetermined position of the outer periphery portion side of the predetermined position P. Temperature sensors 73, 74, and 75 being, for example, thermocouples are each provided at a bottom portion of each of the holes 70, 71, and 72, that is, the portions nearest to a top face of the heating plate 63, so that the temperature of each predetermined position of the heating plate 63 can be measured whenever necessary. The temperature measurement results by the temperature sensors 73 to 75 are sent to the aforementioned heater controller 67 and a defect detector 77 as processing means, and in the heater controller 67, the heater 68 is adjusted so that the heating plate temperature becomes at a predetermined temperature based on the measurement results, while in the defect detector 77, judgement as to whether or not the wafer W is accurately placed at the predetermined position P, which will be described later, that is, judgement as to whether or not the wafer W is judged as a defective product is made based on the measurement results.

Figure 7:
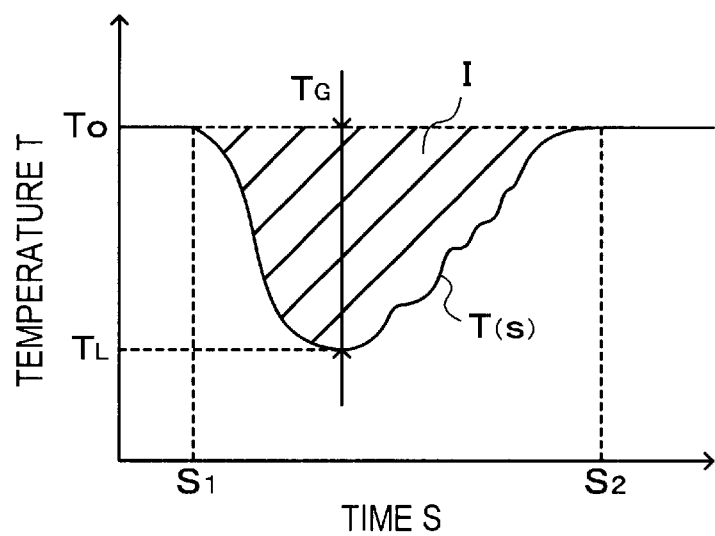
FIG. 7 is an explanatory view showing a temperature integrated area determined by a temperature curve of heating plate temperature when a wafer is placed at the heating plate and a set temperature.

The aforementioned defect detector 77 has the function of calculating an area (the area shown by the oblique lines in FIG. 7) enclosed by a temperature curve T(s) of the heating plate 63 in a predetermine period of time, for example, from a time $S_1$ at which the wafer W is placed over the heating plate 63 as a first point of time to a time $S_2$ at which the heating plate temperature returns to a set temperature $T_0$ as a second point of time, and the set temperature $T_0$ of the heating plate 63, that is a so-called temperature integrated area I, based on the measurement result of each of the temperature sensors 73 to 75. The temperature integrated area I corresponds to the value determined by the following expression (1).

$$I = \int_{S_1}^{S_2} \{T(S) - T_0\} ds \quad (1)$$

The defect detector 77 has the function of storing a threshold value H being an upper limit value and a threshold value L being a lower limit value of an allowable range of the temperature integrated area previously fixed for each of the temperature sensors 73 to 75, and also has the function of comparing the stored threshold values H and L with the measured temperature integrated area I. In the defect detector 77, it is judged that the wafer W is accurately placed when the temperature integrated area I is between the threshold values H and L, and when the temperature integrated area I is a value out of the range from the threshold values H to L, it is judged that the wafer W is not accurately placed, that is, it is judged that the wafer W is a defective product, whereby detection of a defective product is performed. Here, as for the aforementioned threshold values, for example, data of a number of the temperature integrated areas in a case in which the wafer W is accurately placed are collected in advance, and the temperature integrated area corresponding to a standard deviation σ obtained from the data is set as the threshold value H, and the temperature integrated area corresponding to −σ is set as the threshold value L.

The defect detector 77 can perform marking for the wafers W being defective products to distinguish the wafers W judged as defective products from the other wafers W that are conforming products. More specifically, for example, the wafers W to be treated are given numbers in advance, and when the wafer W is judged as a defective product, the number of the wafer W is stored. As for the other marking methods, it may be suitable to mark the defective wafer W so as to distinguish it from conforming products on the software as well as to actually mark the wafer W.

Hoisting and lowering pins 80 for supporting the wafer W when the wafer W is carried in and out and hoisting and lowering the wafer W are provided under the heating plate 63, and the hoisting and lowering pin 80 is structured to be movable up and down by a hoisting and lowering drive mechanism 81. Holes 83 perpendicularly penetrating through the heating plate 63 are provided near a center portion of the heating plate 63, so that the hoisting and lowering pins 80 can penetrate through these holes 83 and protrude above the heating plate 63.

The heating plate housing part 61 has a supporting member 85 for supporting an outer edge portion of the heating plate 63 and a supporting stand 86 for supporting the supporting member 85 as shown in FIG. 4. A heat insulator is used for the supporting member 85 so as to prevent the heat of the heating plate 63 from escaping outside. The supporting stand 86 is formed into an almost cylindrical shape with a top face being opened, and it supports the supporting member 85 on its upper portion.

Further, the heating plate housing part 61 has an almost cylindrical support ring 87 for enclosing the support member 85 and the support stand 86. The support ring 87 is provided with a blow-out port 87a for spouting, for example, an inert gas toward the inside of the treatment chamber S, whereby the inside of the treatment chamber S can be purged. A cylindrical case 88 being an outer circumferential surface of the heating plate housing part 61 is provided outside the support ring 87.

Next, an operation of the PEB unit 44 structured as above will be explained with a photolithography process performed in the coating and developing treatment system 1.

First, the wafer carrier 7 takes one untreated wafer W out of the cassette C and carries it into the adhesion unit 31 included in the third treatment unit group G3. The wafer W coated with an adhesion promoter such as HMDS for enhancing the adhesion to the resist solution in the adhesion unit 31 is carried to the cooling unit 30 by the main carrier unit 13 and cooled to a predetermined temperature. Thereafter, the wafer W is carried to the resist coating unit 17 or 19 and the pre-baking unit 34 or 35 in order to be subjected to predetermined treatments. Thereafter, the wafer W is carried to the extension and cooling unit 41.

Subsequently, the wafer W is taken out of the extension and cooling unit 41 by the wafer carrier 50, and then carried to the aligner (not illustrated) via the periphery exposure unit 51. The wafer W for which the exposure processing is finished is carried to the extension unit 42 by the wafer carrier 50 and thereafter held by the main carrier unit 13. Subsequently, the wafer W is carried to the PEB unit 44 or 45 where heat treatment is performed.

The wafer W for which the heat treatment is finished is carried to the cooling unit 43, the developing treatment unit 18 or 20, the post-baking unit 35, and the cooling unit 30 in order, and the predetermined treatment is performed in each unit. Thereafter, the wafer W is returned to the cassette C by the wafer carrier 7 via the extension unit 32, whereby a series of predetermined coating and developing treatment is finished.

The operation of the aforementioned PEB unit 44 will be explained in detail. First of all, before heat treatment for the wafer W is started, data of the temperature integrated areas at each of the temperature sensors 73, 74 and 75 in the cases in which the wafer W is accurately placed at the predetermined position P are collected as described above, and standard deviations $\sigma_1$, $\sigma_2$ and $\sigma_3$ of the aforementioned temperature integrated areas for each of the temperature sensors 73, 74, and 75 are obtained. Subsequently, the values of the temperature integrated areas corresponding to the standard deviations $\sigma_1$, $\sigma_2$ and $\sigma_3$ are set in the defect detector 77 as threshold values $H_1$, $H_2$, and $H_3$, and the values of the temperature integrated areas corresponding to $-\sigma_1$, $-\sigma_2$ and $-\sigma_3$ are set in the defect detector 77 as threshold values $L_1$, $L_2$, and $L_3$. The heating plate 63 is heated so as to be at the heating set temperature $T_0$, and it is maintained at the set temperature $T_0$ by each of the temperature sensors 73, 74, and 75, and the heater controller 67.

Figure 8:
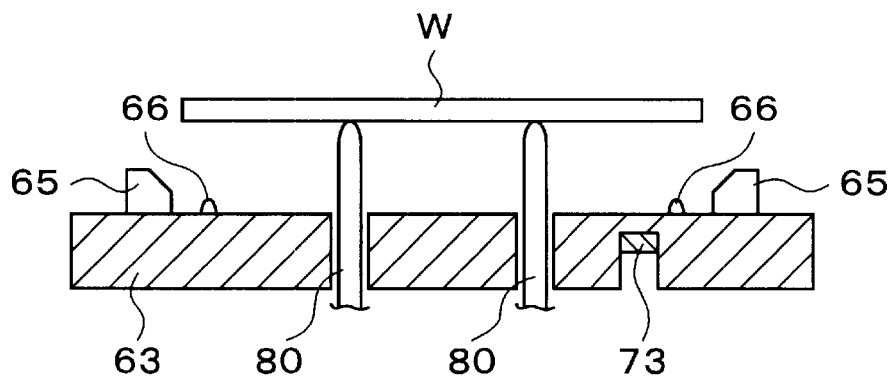
FIG. 8 is an explanatory view showing a state in which the wafer is supported on hoisting and lowering pins.

When the heat treatment is started, monitoring of the heating plate temperature by the temperature sensors 73, 74, and 75 is started, and the measurement results thereof are sent to the defect detector 77 whenever necessary. Subsequently, the lid body 60 is hoisted by a drive mechanism not illustrated, and the wafer W, which has finished the previous step, that is, the exposure processing for the pattern, is carried into the PEB unit 44 by the main carrier unit 13. The wafer W carried into the PEB unit 44 is supported on the hoisting and lowering pins 80 waiting at the predetermined position above the heating plate 63 in advance as shown in FIG. 8.

Subsequently, the lid body 60 is lowered, and integrated with the heating plate housing part 63 to form the treatment chamber S. In this situation, supply of an inert gas is started from the blow-out port 87a of the support ring 87. As a result that the inert gas is exhausted from the exhaust portion 60a through the treatment chamber S, air flow occurs, and the atmosphere inside the treatment chamber S is purged hereinafter until the heat treatment is finished.

Figure 9:
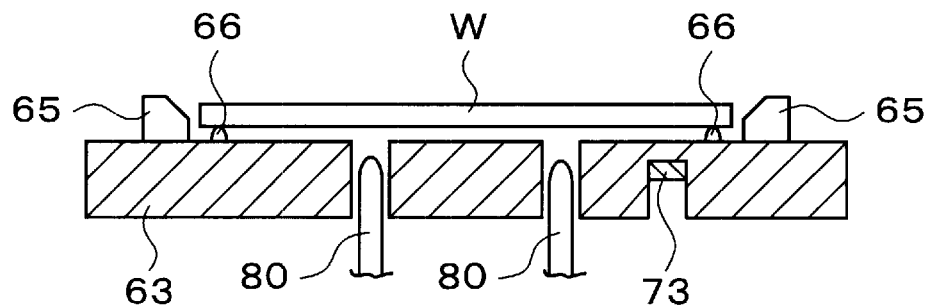
FIG. 9 is an explanatory view showing a state in which the wafer is placed at a predetermined position.

Thereafter, the wafer W is lowered with the hoisting and lowering pins 80 by the hoisting and lowering drive mechanism 81, and it is usually placed on the support pins 66 at the predetermined position P of the heating plate 63 as shown in FIG. 9. At the same time when the wafer W is placed thereat, the heat treatment is started.

The temperature curve $T(s)_1$ of the heating plate 63 at this time temporarily lowers immediately after the wafer W is placed since the heat of the heating plate 63 is taken by the wafer W at a low temperature, and it returns to the set temperature $T_0$ by the heat of the heater 68 again.

Hereinafter, processing of measured data in the defect detector 77 will be explained with the aforementioned measured data sent from the temperature sensor 73 taken as an example. First, the temperature integrated area I enclosed by the aforementioned temperature curve $T(s)_1$ and the set temperature $T_0$ is calculated in the defect detector 77 which receives the measured data from the temperature sensor 73.

Subsequently, the temperature integrated area I is compared with the threshold values $H_1$ and $L_1$ of the temperature integrated area previously set. When the temperature integrated area I is in the range between $H_1$ and $L_1$, it is judged that the wafer W is accurately placed at the predetermined position P over the heating plate 63, and when the temperature integrated area I is not in the range between $H_1$ and $L_1$, it is judged that the wafer W is not accurately placed at the predetermined position P and the wafer W is a defective product. As shown in FIG. 9, when the wafer W is accurately placed at the predetermined position P, the temperature integrated area I is in the range between $H_1$ and $L_1$, and the wafer W is not judged as a defective product.

Figure 10:
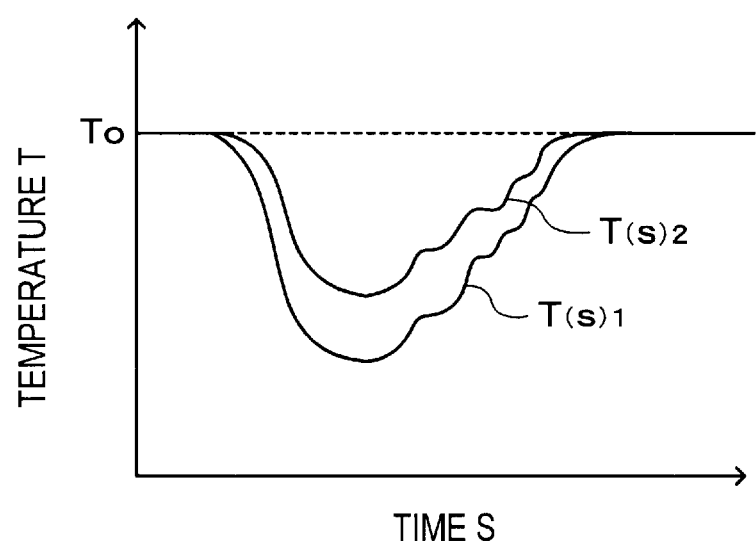
FIG. 10 is a graph showing temperature curves of the heating plate temperature in a case in which the wafer is placed at the predetermined position and in a case in which the wafer is not placed at the predetermined position.
Figure 11:
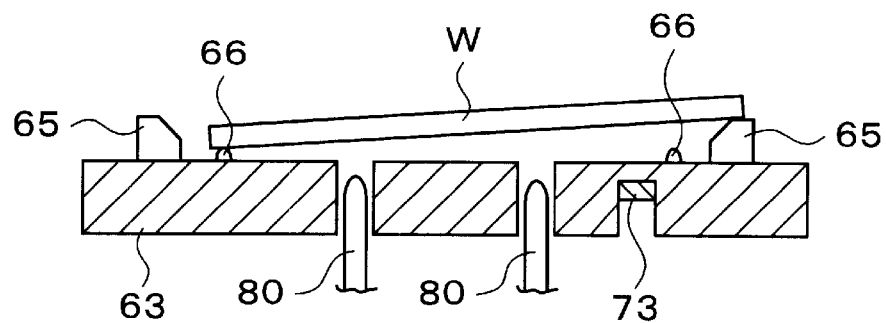
FIG. 11 is an explanatory view showing a state in which the wafer is placed to ride on the guide member.

Meanwhile, for example, when the wafer W is placed to ride on the guide members 65 as shown in FIG. 11, and the distance between the heating plate 63 and the wafer W becomes longer than usual, the temperature curve $T(s)_2$ of the heating plate 63 after the wafer W is placed shows less reduction in the heating plate temperature by the wafer W as compared with when the wafer W is accurately placed (the temperature curve $T(s)_1$) as shown in FIG. 10. Accordingly, in such a case, the temperature integrated area I becomes smaller, and if it is smaller than the threshold value L, the wafer W is judged as a defective product.

The measurement data from the other temperature sensors 74 and 75 are similarly processed, and defective products of the wafers W are detected based on the data of each of the temperature sensors 74 and 75. Accordingly, unless the wafer is accurately placed at all the predetermined positions at which the temperature sensors 73, 74, and 75 are placed, the wafer W is judged as a defective product.

Next, when the wafer W is judged as a defective product, marking for indicating that the wafer W is a defective product is performed. Subsequently, regardless of whether it is a defective product or not, heat treatment for a predetermined period of time is continued as it is. After a lapse of the predetermined heating time, the wafer W is hoisted by the hoisting and lowering pins 80 again, and heating by the heating plate 63 is finished. Subsequently, the lid body 60 is hoisted again and the treatment chamber S is opened. The wafer W is then transferred to the main carrier unit 13 from the hoisting and lowering pins 80, and is carried out of the PEB unit 44, whereby a series of heat treatment is finished.

After a series of coating and developing treatment is finished as described above, the marked wafer W is distinguished form the other wafers W, so that the defective product is removed from the conforming products.

According to the above-described embodiment, it is judged whether the wafer W is accurately placed or not by paying attention to a change in the heating plate temperature immediately after the wafer W is placed to make it possible to detect the defective products of the wafers W, thus making it possible to perform the detection more rapidly as compared with the prior art.

Further, the temperature integrated area I determined by the range enclosed by the temperature curve $T(s)$ after the wafer W is placed over the heating plate 63, which is measured by each of the temperature sensors 73, 74, and 75, and the set temperature $T_0$ is calculated, and the temperature integrated area I is compared with the threshold values H and L which are previously set, thus reducing the variation in the data as compared with, for example, the case in which comparison is made with the lowest temperature of the heating plate temperature as a reference, which makes it possible to make more reliable judgement.

Furthermore, since the threshold values H and L are related to the standard deviation, the data required when the threshold values H and L are obtained is only one kind of data, that is, it is sufficient that the data of the temperature integrated area only in the case in which the wafer W is accurately placed at the predetermined position is collected, and it is not necessary to collect the data of both cases in which the wafer W is accurately placed and not accurately placed.

In the above embodiment, it is judged whether or not the wafer W is accurately placed with the temperature integrated area I as a reference, and the threshold values at this time are related to the standard deviation, but it is naturally suitable to make judgement with the temperature integrated area I as a reference without using the standard deviation as the threshold values, or it may be suitable to use the standard deviation as the threshold values without using the temperature integrated area I as the reference.

In the former case, it is proposed that the data of the temperature integrated areas of both cases in which, for example, the wafer W is accurately placed and it is placed to deviate from the predetermined position P are collected and the border line is used as the threshold value. In this case, more reliable judgement can be also made since the temperature integrated area is used as the reference.

In the latter case, it is proposed that the value of the measured heating plate temperature is used as the reference as it is instead of the temperature integrated area I. In such a case, for example, the lowest temperature $T_L$ (shown in FIG. 7) when the heating temperature reduces is compared with the standard deviation $\sigma_L$ as a threshold value which is determined from the lowest temperature of the heating plate when the wafer W is accurately placed, which is collected in advance, and when $T_{L<-\sigma L}$, and $\sigma_L<T_L$, it is judged that the wafer W is not accurately placed, and the wafer W treated at this time is recognized as a defective product. In this case, the standard deviation is also used as the threshold value, thus making it easy to collect the data when setting the threshold value and reducing the working time and effort.

Further, maximum temperature difference $T_G$ (shown in FIG. 7) being the difference between the heating plate set temperature $T_0$ and the lowest temperature $T_L$ when the temperature of the heating plate 63 reduces to the lowest may be used instead of the lowest temperature $T_L$. In this case, it is also judged whether the wafer W is properly placed or not by comparing it with the standard deviation being the threshold value previously set as in the case of using the lowest temperature $T_L$, thus making it possible to reduce time and effort in obtaining the threshold value.

Furthermore, in the above-described embodiment, the heating plate temperature is measured at the three spots, but this is not limited to the three spots, and it may be measured at one spot, or at a plurality of spots other than three. The threshold values are set for each fixed position for temperature measurement, but one threshold value common to all the temperature measurement positions may be set, so that it may be judged whether or not the wafer W is properly placed with the threshold value as the reference.

Figure 12:
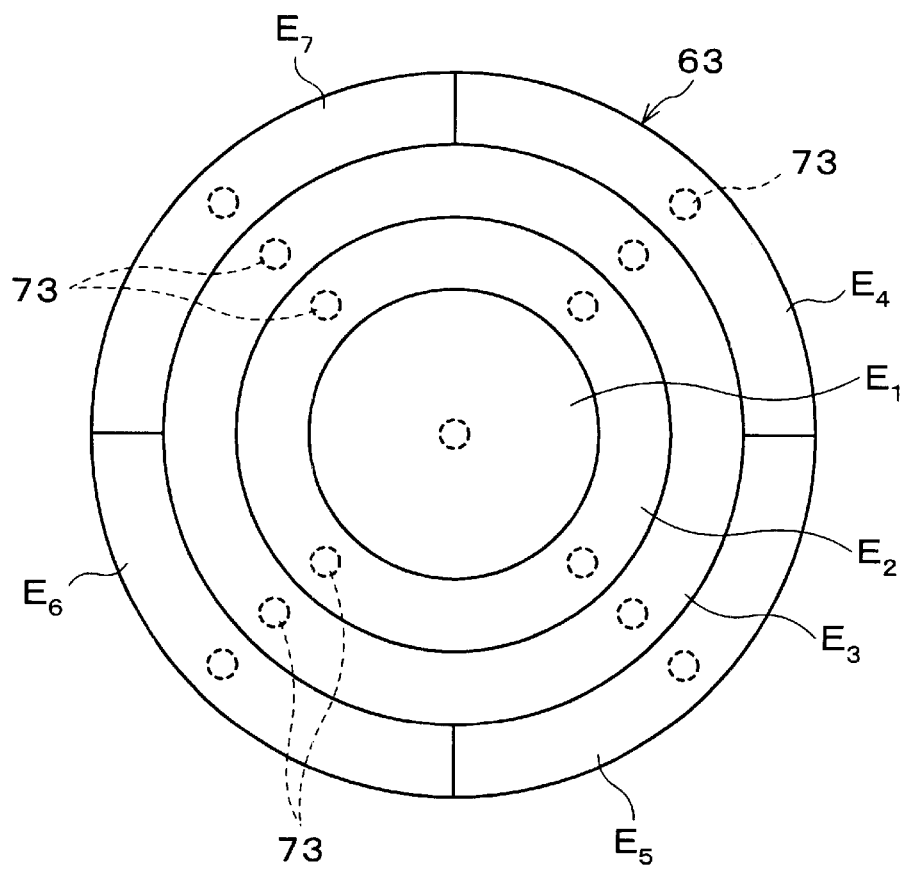
FIG. 12 is a plan view in a case in which a heating area of the heating plate is divided.
Figure 13:
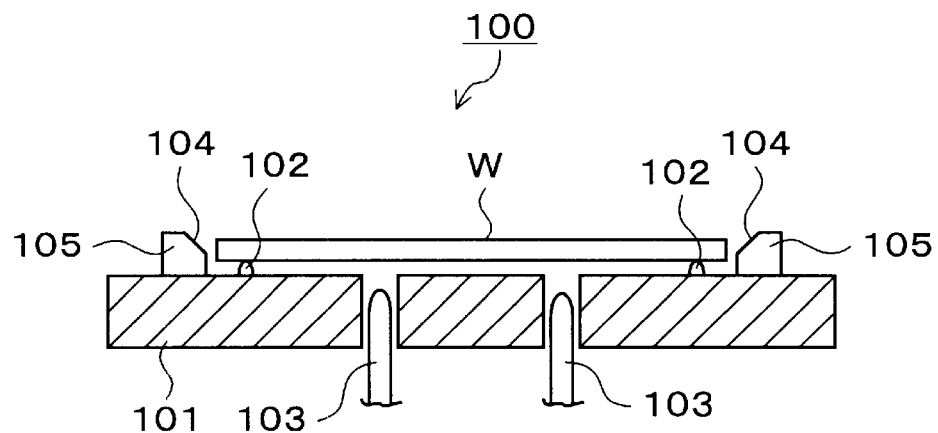
FIG. 13 is an explanatory view of a vertical section schematically showing a structure of an ordinary heating plate.
Figure 14:
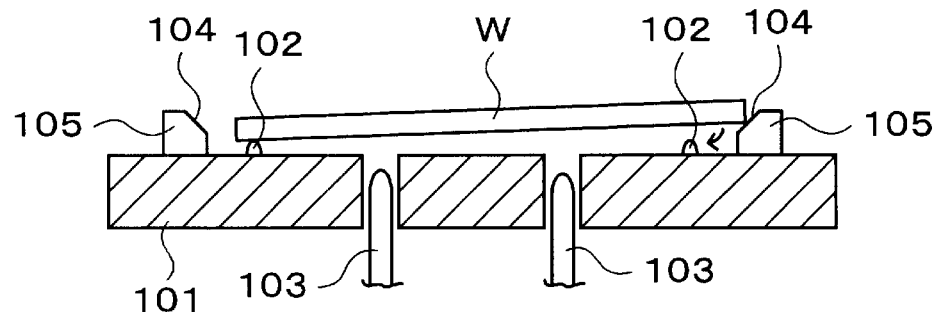
FIG. 14 is an explanatory view showing a state in which the wafer is placed on an inclined plane of the guide member.

For example, as shown in FIG. 12, the heating plate 63 is structured so that heating of the single heating plate 63 is divided into a plurality of areas, for example, into seven areas E1 to E7 to make the temperature of the heating plate controllable for each of the areas E1 to E7.

In this case, a single or a plurality of temperature sensors 73 is or are provided for each of the areas E1 to E7. Subsequently, the temperature integrated area as described above may be obtained for each of the areas E1 to E7 and compared with those of the other areas of E1 to E7, and thereby it may be judged whether or not the wafer W is properly placed.

For example, when the wafer W rides on dust on the heating plate 63, and for example, when the dust is in the area E3, the temperature integrated area of the area E3 naturally and obviously shows a value greatly different from those of the other areas.

Consequently, in such a case, it is judged that the wafer W is not accurately placed at the predetermined position of the heating plate 63.

In the aforementioned embodiment, as a measure taken after the wafer W is judged as defective, heat treatment is continued and the wafer W is marked, but, for example, a speaker for giving a warning or an input section for inputting an instruction of an operator may be connected to the defect detector 77, and when the wafer W is judged as a defective product, an alarm may be given so that the operator gives the instruction of the measure to the warning through the input section. The instruction of the operator may intend to discontinue or continue the heat treatment. The heat treatment may be discontinued immediately at the point of time when the wafer W is judged as a defective product.

In many cases in which the wafer W is not accurately placed, the reason is the positional deviation of the main carrier unit 13 from the hoisting and lowering pins 80, and when the wafer W is judged as an defective product, the position of the main carrier unit 13 may be corrected.

The processing apparatus according to the above embodiment is about the PEB unit 44 or 45, but it is applicable in the other heat treatment unit, for example, the pre-bake unit 33 or 34, or the post-bake unit 46 or 47.

It is also applicable to the cooling treatment unit having a heating plate for cooling the wafer W placed over it. In the case of the cooling treatment unit, the wafer W placed over it has higher temperature than that of the heating plate, and therefore when the wafer W is placed over the heating plate, the heating plate temperature rises temporarily and thereafter is returned to the set temperature of the heating plate. When the wafer W is not accurately placed at the predetermined position, the temperature rise is small. Accordingly, by using the difference in the temperature rise, it can be judged whether or not the wafer W is accurately placed over the heating plate with use of the temperature integrated area I and the like as in the aforementioned heat treatment unit.

The embodiment explained above is about the processing apparatus for the wafer W in the photolithography process in the semiconductor device fabrication, but the present invention is also applicable to a processing apparatus for substrates other than a semiconductor wafer, for example, an LCD substrate.

According to the present invention, it is judged whether or not a substrate is accurately placed and the substrate is properly heat-treated based on a temperature change of the plate when the substrate is placed over the plate, thus making it possible to detect the defect of the substrate at the earlier step. Accordingly, production of many defective substrates is prevented during a time period until a defective is detected, thus enhancing yield.

According to the present invention, it is judged whether the substrate is placed at the predetermined position with the temperature integrated area I as the reference, thus making it possible to make judgement with fewer variations and more reliability than when the heating plate temperature is used as the reference as it is.

Further, according to the present invention, since the values related to the standard deviation are used as the threshold values, only one kind of data must be collected in advance, that is, only the data when the substrate is accurately placed must be collected, thus reducing the working time and effort.

What is claimed is:

1. A method of judging whether a substrate is accurately placed at a predetermined position when placing the substrate at the predetermined position on a plate to perform heat treatment or cooling treatment therefor, comprising:

the step of setting said plate at a predetermined temperature;

the step of measuring temperature of the plate at least from a first point of time to a second point of time during which the plate temperature changes, after placing the substrate at said plate;

the step of calculating a temperature integrated area I determined by a range enclosed by the measured temperature curve changing in time sequence and a set temperature of said plate; and the step of comparing the calculated temperature integrated area I with a threshold value of a temperature integrated area previously set.

2. A judging method as set forth in claim 1,
wherein the threshold values of the temperature integrated threshold value is related to standard deviation of the temperature integrated area when the substrate is accurately placed at the predetermined position.

3. A judging method as set forth in claim 1,
wherein said temperature measurement is performed at a plurality of positions on the plate, and said comparing step is performed for each measurement position.

4. A judging method as set forth in claim 1,
wherein on said plate, guiding members for guiding the substrate when the substrate is placed are provided to surround the predetermined position.

5. A method of judging whether a substrate is accurately placed at a predetermined position when placing the substrate at the predetermined position on a plate to perform heat treatment or cooling treatment therefor, comprising:

the step of setting said plate at a predetermined temperature;

the step of measuring temperature of the plate at least from a first point of time to a second point of time during which the plate temperature changes, after placing the substrate on said plate; and the step of comparing the measured temperature with threshold values related to standard deviation of the plate temperature in a case in which the substrate is accurately placed.

6. A method of judging whether a substrate is accurately placed at a predetermined position when placing the substrate at the predetermined position on a plate to perform heat treatment or cooling treatment therefor, comprising:

the step of setting said plate at a predetermined temperature;

the step of measuring temperature of the plate at least from a first point of time to a second point of time during which the plate temperature changes, after placing the substrate at said plate; and the step of comparing a maximum temperature difference of the measured temperature with previously set threshold values related to standard deviation of a maximum temperature difference of the plate temperature in a case in which the substrate is accurately placed.

7. A processing apparatus having a plate for placing a substrate at a predetermined position to heat or cool the substrate at a predetermined temperature, comprising:

a temperature sensor for measuring temperature of said plate; and a processor for calculating a temperature integrated area I determined by a range enclosed by the measured temperature curve changing in time sequence and set temperature of said plate based on measurement result of plate temperature from a first point of time after the substrate is placed at said plate to a second point of time during which the plate temperature changes, which is measured by said temperature sensor, and for comparing the temperature integrated area I with threshold values of a temperature integrated area previously set.

8. A processing apparatus as set forth in claim 7,
wherein a plurality of said temperature sensors are provided on the plate, and said processing means performs the calculation of the temperature integrated area I and the comparison of the temperature integrated area I with the threshold values for a measurement result of each temperature sensor.

9. A processing apparatus as set forth in claim 7,
wherein on said plate, guiding members for guiding the substrate when the substrate is placed are provided to surround the predetermined position.

10. A processing apparatus having a plate for placing a substrate at a predetermined position to heat or cool the substrate at a predetermined temperature, comprising:

a temperature sensor for measuring temperature of said plate; and means for comparing measured temperature of said temperature sensor with previously set threshold values related to standard deviation of plate temperature in a case in which the substrate is accurately placed.

11. A processing apparatus as set forth in claim 10,
wherein a plurality of said temperature sensors are provided on the plate, and said comparing means performs the comparison for a measurement result of each of the temperature sensors.

12. A processing apparatus having a plate for placing a substrate at a predetermined position to heat or cool the substrate at a predetermined temperature, comprising:

a temperature sensor for measuring temperature of said plate; and means for comparing a maximum temperature difference of measured temperature of said temperature sensor with previously set threshold values related to standard deviation of a maximum temperature difference of the plate temperature in a case in which the substrate is accurately placed.

13. A processing apparatus as set forth in claim 12,
wherein a plurality of said temperature sensors are provided on the plate, and said comparing means performs the comparison for a measurement result of each of the temperature sensors.

* * * * *